US010101429B2

(12) United States Patent
Deng et al.

(10) Patent No.: US 10,101,429 B2
(45) Date of Patent: Oct. 16, 2018

(54) ACOUSTIC TRANSMISSION DEVICE AND PROCESS FOR TRACKING SELECTED HOSTS

(71) Applicant: Battelle Memorial Institute, Richland, WA (US)

(72) Inventors: Zhiqun Deng, Richland, WA (US); Huidong Li, Richland, WA (US); Jun Lu, Richland, WA (US); Mitchell J. Myjak, Richland, WA (US); Jayson J. Martinez, Richland, WA (US); Jie Xiao, Richland, WA (US); Richard S. Brown, Richland, WA (US); Samuel S. Cartmell, Richland, WA (US)

(73) Assignee: Battelle Memorial Institute, Richland, WA (US)

(*) Notice: Subject to any disclaimer, the term of this patent is extended or adjusted under 35 U.S.C. 154(b) by 494 days.

(21) Appl. No.: 14/631,587

(22) Filed: Feb. 25, 2015

(65) Prior Publication Data

US 2016/0245894 A1    Aug. 25, 2016

(51) Int. Cl.
*G01S 1/72* (2006.01)
*G01S 5/18* (2006.01)
(Continued)

(52) U.S. Cl.
CPC .............. *G01S 1/72* (2013.01); *A01K 11/006* (2013.01); *A01K 61/90* (2017.01); *A61B 5/0015* (2013.01);
(Continued)

(58) Field of Classification Search
CPC ........ A61B 8/06; G01S 7/524; H02M 1/4208; H02M 1/44; H02M 2001/0029;
(Continued)

(56) References Cited

U.S. PATENT DOCUMENTS 3,100,886 A * 8/1963 Marks ................... B06B 1/0269
                                                            310/317
3,262,093 A * 7/1966 Junger .................. B06B 1/0655
                                                            367/159
(Continued)

FOREIGN PATENT DOCUMENTS

CA    2091043    9/1994
CN    1424592    6/2003
(Continued)

OTHER PUBLICATIONS

Gallego-Juarez; NPL, Non Patent Literature; (Experimental study of nonlinearity in free progessive accoustic waves in air at 20 kHz; Jan. 1, 1979).*
(Continued)

*Primary Examiner* — Isam A Alsomiri
*Assistant Examiner* — Amie M Ndure
(74) *Attorney, Agent, or Firm* — Wells St. John P.S.

(57) ABSTRACT

A new acoustic tag and process are disclosed for identifying and tracking underwater hosts in up to three dimensions. The acoustic tag has an operation lifetime up to a year or longer at a pulse rate interval of about 15 seconds. The acoustic tag has a signal detection range up to at least about 500 meters that enhances detection probability.

27 Claims, 6 Drawing Sheets

(51) Int. Cl.
*A61B 5/07* (2006.01)
*G06K 17/00* (2006.01)
*H04B 1/034* (2006.01)
*A01K 11/00* (2006.01)
*A61B 5/00* (2006.01)
*A61B 5/11* (2006.01)
*A01K 61/90* (2017.01)
*G06K 19/07* (2006.01)

(52) U.S. Cl.
CPC .............. *A61B 5/07* (2013.01); *A61B 5/1112* (2013.01); *G01S 5/18* (2013.01); *G06K 17/00* (2013.01); *H04B 1/034* (2013.01); *A61B 2503/40* (2013.01); *A61B 2562/08* (2013.01); *G06K 19/0728* (2013.01)

(58) Field of Classification Search
CPC ........ H02M 3/073; H02P 25/04; H02P 25/08; H04B 1/034; H04B 1/086; Y02B 70/126; Y10S 367/903
See application file for complete search history.

(56) References Cited

U.S. PATENT DOCUMENTS

| | | | |
|---|---|---|---|
| 3,311,830 A * | 3/1967 | Skirvin | H03C 5/00 332/120 |
| 3,576,732 A | 4/1971 | Weidinger et al. | |
| 3,713,086 A | 1/1973 | Trott | |
| 4,042,845 A | 8/1977 | Hackett | |
| 4,241,535 A | 12/1980 | Tsukuda | |
| 4,259,415 A | 3/1981 | Tamura et al. | |
| 4,353,004 A * | 10/1982 | Kleinschmidt | G01S 7/524 310/317 |
| 4,762,427 A | 8/1988 | Hori et al. | |
| 4,986,276 A * | 1/1991 | Wright | A61B 8/06 600/437 |
| 5,177,891 A | 1/1993 | Holt | |
| 5,211,129 A | 5/1993 | Taylor et al. | |
| 5,344,357 A | 9/1994 | Lyczek | |
| 5,517,465 A | 5/1996 | Nestler et al. | |
| 5,675,555 A | 10/1997 | Evans et al. | |
| 5,697,384 A | 12/1997 | Miyawaki et al. | |
| 5,974,304 A * | 10/1999 | Chen | H04B 1/086 455/351 |
| 5,995,451 A | 11/1999 | Evans et al. | |
| 6,201,766 B1 | 3/2001 | Carlson et al. | |
| 6,662,742 B2 | 12/2003 | Shelton et al. | |
| 6,712,772 B2 | 3/2004 | Cohen et al. | |
| 7,016,260 B2 | 3/2006 | Baray | |
| 7,289,931 B2 | 10/2007 | Ebert | |
| 7,457,720 B2 | 11/2008 | Ebert | |
| 8,032,429 B2 | 10/2011 | Shafer | |
| 8,033,890 B2 | 10/2011 | Warner et al. | |
| 8,564,985 B2 * | 10/2013 | van Straaten | H02M 1/44 363/60 |
| 9,266,591 B2 | 2/2016 | Lu | |
| 2003/0117893 A1 | 6/2003 | Bary | |
| 2003/0128847 A1 * | 7/2003 | Smith | A61B 7/04 381/67 |
| 2006/0218374 A1 | 9/2006 | Ebert | |
| 2007/0088194 A1 | 4/2007 | Tahar et al. | |
| 2007/0103314 A1 | 5/2007 | Geissler | |
| 2007/0288160 A1 | 12/2007 | Ebert | |
| 2009/0073802 A1 | 3/2009 | Nizzola et al. | |
| 2009/0079368 A1 * | 3/2009 | Poppen | H02M 1/4208 318/254.1 |
| 2009/0188320 A1 * | 7/2009 | Greenough | G01N 29/11 73/602 |
| 2011/0105829 A1 | 5/2011 | Ball | |
| 2011/0163857 A1 | 7/2011 | August et al. | |
| 2011/0181399 A1 | 7/2011 | Pollack et al. | |
| 2011/0254529 A1 * | 10/2011 | van Straaten | H02M 1/44 323/311 |
| 2012/0134239 A1 | 5/2012 | Struthers | |
| 2012/0277550 A1 | 11/2012 | Rosenkranz et al. | |
| 2013/0012865 A1 | 1/2013 | Sallberg et al. | |
| 2013/0181839 A1 | 7/2013 | Cao | |
| 2013/0324059 A1 | 12/2013 | Lee et al. | |
| 2014/0211594 A1 | 7/2014 | Allen et al. | |
| 2015/0063072 A1 | 3/2015 | Deng et al. | |
| 2015/0241566 A1 | 8/2015 | Chakraborty et al. | |
| 2015/0289479 A1 | 10/2015 | Allen et al. | |
| 2016/0211924 A1 | 7/2016 | Deng et al. | |
| 2017/0089878 A1 | 3/2017 | Deng et al. | |
| 2017/0164581 A1 | 6/2017 | Deng et al. | |
| 2017/0170850 A1 | 6/2017 | Deng et al. | |
| 2018/0055007 A1 | 3/2018 | Deng et al. | |

FOREIGN PATENT DOCUMENTS

| | | |
|---|---|---|
| CN | 102568463 | 7/2012 |
| CN | 102598716 | 7/2012 |
| CN | 202414143 | 9/2012 |
| CN | 102754249 | 10/2012 |
| CN | 2014800479315 | 7/2017 |
| EP | 2037396 A1 | 3/2009 |
| EP | 1705508 B1 | 6/2010 |
| GB | 1195633 A | 6/1970 |
| GB | 2188028 A | 9/1987 |
| WO | WO 95/03691 | 2/1995 |
| WO | WO 2011/068825 | 6/2011 |
| WO | WO 2011/079338 | 7/2011 |
| WO | WO 2015/031853 | 3/2015 |
| WO | WO PCT/US2014/053578 | 3/2015 |
| WO | WO PCT/US2015/062200 | 2/2016 |
| WO | WO PCT/US2014/053578 | 3/2016 |
| WO | WO PCT/US2016/054961 | 11/2016 |
| WO | WO PCT/US2016/054981 | 11/2016 |
| WO | WO PCT/US2016/055045 | 2/2017 |
| WO | WO PCT/US2015/062200 | 8/2017 |
| WO | WO PCT/US2017/038082 | 9/2017 |
| WO | WO PCT/US2017/038082 | 11/2017 |
| WO | WO PCT/US2016/054981 | 6/2018 |
| WO | WO PCT/US2016/055045 | 6/2018 |

OTHER PUBLICATIONS

American Fisheries Society, hereinafter known as "ASF"; NPL (The Juvenile Salmon Acoustic Telemetry System: A New Tool; vol. 35 No. 1. Jan. 2010, www.fisheries.org).*

Brown, R. S., et al., An Evaluation of the Maximum Tag Burden for Implantation of Acoustic Transmitters in Juvenile Chinook Salmon, North American Journal of Fisheries Management, 30, 2010, 499-505.

Deng, Z., et al., Design and Instrumentation of a Measurement and Calibration System for an Acoustic Telemetry System, Sensors, 10, 2010, 3090-3099.

Deng, Z. D., et al., A Cabled Acoustic Telemetry System for Detecting and Tracking Juvenile Salmon: Part 2. Three-Dimensional Tracking and Passage Outcomes, Sensors, 11, 2011, 5661-5676.

Lam, P., et al., Physical characteristics and rate performance of (CFx)n (0.33<x<9,66) in lithium batteries, Journal of Power Sources, 153, 2006, 354-359.

McMichael, G. A., et al., The Juvenile Salmon Acoustic Telemetry System: A New Tool, Fisheries, 35, 2010, 9-22.

Meduri, P., et al., Hybrid CVx-Ag2V4O11 as a high-energy, power

(56) References Cited

OTHER PUBLICATIONS density cathode for application in an underwater acoustic microtransmitter, Electrochemistry Communications, 13, 2011, 1344-1348.
Ritchie, A. G., et al., Further development of lithium/polycarbon monofluoride envelope cells, Journal of Power Sources, 96, 2001, 180-183.
Weiland, M. A., et al., A Cabled Acoustic Telemetry System for Detecting and Tracking Juvenile Salmon: Part 1. Engineering Design and Instrumentation, Sensors, 11, 2011, 5645-5660.
Zhang, S. S., et al., Enhancement of discharge performance of Li/CFx cell by thermal treatment of CFx cathode material, Journal of Power Sources, 188, 2009, 601-605.
Yazami, R., et al., Fluorinated carbon nanofibres for high energy and high power densities primary lithium batteries, Electrochemistry Communications, 9, 2007, 1850-1855.
Li, H., et al., Piezoelectric Materials Used in Underwater Acoustic Transducers, Sensor Letters, 10 (3/4), 2012a, 679-697.
Li, H., et al., Design Parameters of a Miniaturized Piezoelectric Underwater Acoustic Transmitter, Sensors, 12, 2012, 9098-9109.
Rub, A. M. W, et al., Comparative Performance of Acoustic-Tagged and Passive Integrated Transponder-Tagged Juvenile Salmonids in the Columbia and Snake Rivers, 2007, U.S. Army Corps of Engineers, Portland District, Portland, Oregon.
Eppard, B., Juvenile Salmon Acoustic Telemetry Systems JSATS, Dec. 14, 2011, URL:https://www.nwcouncil.org/media/23478/jsats.pdf, 1-13.
Biopack Systems, Inc. Hardware Guide, 2013, 1-152.
Invitation to Pay Additional Fees/Communication Relating to the Results of the Partial International Search for International Application No. PCT/U52014/053578, International Filing Date Aug. 29, 2012, dated Dec. 5, 2014.
Adams et al., "Effects of Surgically and Gastrically Implanted Radio Transmitters on Swimming Performance and Predator Avoidance of Juvenile Chinook Salmon (*Oncorhynchus tshawytscha*)", Canadian Journal of Fisheries and Aquatic Sciences 55, 1998, Canada, pp. 791-797.
Anglea et al., "Effects of Acoustic Transmitters on Swimming Performance and Predator Avoidance of Juvenile Chinook Salmon", North American Journal of Fisheries Management 24, 2004, United States, pp. 162-170.
Atlantic States Marine Fisheries Commision, "American Eel Benchmaek Stock Assessment Report No. 12-01", May 2012, United States, 340 pages.
Bams, "Differences in Performance of Naturally and Artifically Propagated Sockeye Salmon Migrant Fry, as Measured With Swimming and Predation Tests", Journal of the Fisheries Board of Canada 24(5), 1967, Canada, pp. 1117-1153.
Barbin et al., "Behaviour and Swimming Performance of Elvers of the America Eel, Anguilla Rostrata, in an Experiment Flume", Journal of Fish Biology 45, 1994, United Kingdom, pp. 111-121.
Boubee et al., "Downstream Passage of Silver Eels at a Small Hydroelectric Facility", Fisheries Management and Ecology vol. 13, 2006, United Kingdom, pp. 165-176.
Brett, "The Respiratory Metabolism and Swimming Performance of Young Sockeye Salmon", Journal of the Fisheries Board of Canada 21(5), 1964, Canada, pp. 1183-1226.
Brown et al., "Evidence to Challenge the "2% Rule" for Biotelemtry", North American Journal of Fisheries Management 19, 1999, United States, pp. 867-871.
Brown et al., "Survival of Seaward-Migrating PIT and Acoustic-Tagged Juvenile Chinook Salmon in the Snake and Columbia Rivers: An Evaluation of Length-Specific Tagging Effects", Animal Biotelemetry 1:8, 2013, United States, 13 pages.
Collins et al., "Intracoelomic Acoustic Taggin of Juvenile Sockeye Salmon: Swimming Performance, Survival, and Postsurgical Wound Healing in Freshwater and during a Transistion to Seawater", Transaction of the American Fisheries Society 142, 2013, United States, pp. 515-523.
Cote et al., "Swimming Performance and Growth Rates of Juvenile Atlantic Cod Intraperltoneally Implanted with Dummy Acoustic Transmitters", North American Journal of Fisheries Management vol. 19, 1999, United States, pp. 1137-1141.
Counihan et al., "Influence of Extemally Transmitters on the Swimming Performance of Juvenile White Sturgeon", Transactions of the American Fisheries Society 128, 1999, United States, pp. 965-970.
Deng et al., U.S. Appl. No. 15/393,617, filed Dec. 29, 2016, titled "Systems and Methods for Montoring Organism Within an Aquatic Environment", 49 pages.
Fisheries and Oceans Canada (DFO), "Recovery Potential Assessment of American Eel (*Anguilla rostrata*) in Eastern Canada", Canadian Science Advisory Secretarist Science Advisory Report 2013/078, 2013, Canada, 65 pages.
Harrish et al., "A Review of Polymer-Based Water Conditioners for Reduction of Handling-Related Injury", Reviews in Fish Biology and Fisheries 21, 2011, Netherlands, pp. 43-49.
Janak et al., "The Effects of Neutrally Buoyant, Externally Attached Transmitters on Swimming Performance and Predator Avoidance of Juvenile Chinook Salmon", Transactions of the American Fishiers Society 141, 2012, United States, pp. 1424-1432.
MacGregor et al., "Recovery Strategy for the American Eel (*Angullia rostrata*) in Ontario", Ontario Recovery Strategy Series, Prepared for Ontatio Ministry of Natural Resources, Peterborough, Ontario, 2012, Canada, 131 pages.
McGrath et al., "Studies of Upstream Migrant American Eels at the Moses-Saunders Power Dam on the St. Lawrence River near Massena, New York", American Fisheries Society Symposium 33, 2003, United States, pp. 153-166.
Mesa et al., "Survival and Growth of Juvenile Pacific Lampreys Tagged with Passive Integrated Transponders (PUT) in Freshwater and Seawater", Transactions of the American Fisheries Society 141, 2012, United States, pp. 1260-1268.
Mueller et al., "Tagging Juvenile Pacific Lamprey with Passive Integrated Transponders: Methodology, Short-Term Mortality, and Influence on Swimming Performance", North American Journal of Fisheries Management vol. 26, 2006, United States, pp. 361-366.
Normandeau, "Survey for Upstream American Eel Passage at Holyoke Dam, Connecticut River, Massachusetts, 2006", Prepared for Holyoke Gas and Electric by Normandeau Associates, Inc., Apr. 26, 2007, United States, 68 pages.
Økland et al., "Recommendations on Size and Position of Surgically and Gastrically Implanted Electronic Tags in European Silver Eel", Animal Biotelemetry 1:6, 2013, United Kingdom, pp. 1-5.
Panther et al., "Influence of Incision Location on Transmitter Loss, Healing, Survival, Growth, and Suture Retention of Juvenile Chinook Salmon", Transactions of the American Fisheries Society 140, 2011, United States, pp. 1492-1503.
Summerfelt et al., "Anesthesis, Surgery, and Related Techniques", in Schreck, C.B., Moyle, P.B., (Eds.), Methods for Fish Biology, American Fisheries Society, 1990, United States, pp. 213-272.
Verdon et al., "Recruitment of American Eels in the Richelieu River and Lake Champlain: Provision of Upstream Passage as a Regional-Scale Solution to a Large-Scale Problem", American Fisheries Society Symposium 33, 2003, United States, pp. 125-138.
Walker et al., "Effects of a Novel Acoustic Transmitter on Swimming Performance and Predator Avoidance of Juvenile Chinook Salmon: Determination of a Size Threshold", Fisheries Research 176, 2016, Netherlands, pp. 48-54.
Ward et al., "A Laboratory Evaluation of Tagging-Related Mortality and Tag Loss in Juvenile Humpback Chub", North American Journal of Fisheries Management 35, 2015, United States, pp. 135-140.
Wuenschel et al., "Swimming Ability of Eels (*Anguilla rostrata, Conger oceanicus*) at Estuarine Ingress: Contrasting Patterns of Cross-Shelf Transport?", Marine Biology 154, 2008, Germany, pp. 775-786.
Zale et al., "Effects of Surgically Implanted Transmitter Weights on Growth and Swimming Stamina of Small Adult Westslope Cutthroat Trout", Transactions of the American Fisheries Society vol. 134(3), 2005, United States, pp. 653-660.
Aktakka et al., "Energy Scavenging from Insect Flight", Journal of Micromechanics and Microengineering vol. 21, 095016, 2011, United Kingdom, 10 pages.

(56) References Cited

OTHER PUBLICATIONS

Cha et al., "Energy Harvesting from a Piezoelectric Biomimetic Fish Tail", Renewable Energy vol. 86, 2016, Netherlands, pp. 449-458.
Cha et al., "Energy Harvesting from the Tail Beating of a Carangiform Swimmer using Ionic Polymer-Metal Composites ", Bioinspiration and Biomimetics vol. 8, 2013, United Kingdom, 15 pages.
Cook et al., "A Compasrison of Implantation Methods for Large PIT Tags or Injectable Acoustic Transmitters in Juvenile Chinook Salmon", Fisheries Research vol. 154, 2014, Netherlands, pp. 213-223.
Degdeviren et al., "Conformal Piezoelectric Energy Harvesting and Storage from Motions of the Heart, Lung, and Diaphragm", Proceesings of the National Academy of Sciences of the United States of America vol. 111, 2014, United States, pp. 1927-1932.
Deng et al., "An Injectable Acoustic Transmitter for Juvenile Salmon", Scientific Reports, Jan. 29, 2015, United Kingdom, 6 pages.
Deng et al., U.S. Appl. No. 62/267,738, filed Dec. 15, 2015, titled "Transmitters for Animals and Methods for Transmitting from Animals", 42 pages.
Deng et al., U.S. Appl. No. 62/267,797, filed Dec. 15, 2015, titled "Signal Transmitter and Methods for Transmitting Signals from Animals", 34 pages.
Erturk et al., "Underwater Thrust and Power Generation Using Flexible Piezoelectric Composites: An Experimental Investigation Toward Self-Powered Swimmer-Sensor Platforms", Smart Materials and Structures vol. 20, 125013, 2011, United Kingdom, 11 pages.
Hwang et al., "Self-Powered Cardiac Pacemaker Enabled by Flexible Single Crystalline PMN-PT Piezoelectric Energy Harvester", Advanced Materials vol. 26, 2014, Germany, pp. 4880-4887.
Hwang et al., "Self-Powered Deep Brain Stimulation via a Flexible PIMNT Energy Harvester", Energy and Environmental Science vol. 8, 2015, United Kingdom, pp. 2677-2684.
Li et al., "Energy Harvesting from Low Frequency Applications using Piezoelectric Materials", Applied Physics Reviews 1, 041301, 2014, United States, 20 pages.
Li et al., "Piezoelectric Materials Used in Underwater Acoustic Transducers" Sensor Letters vol. 10 (3/4), 2012, United States, pp. 679-697.
Li et al., "Piezoelectric Transducer Design for a Miniaturized Injectable Acoustic Transmitter", Smart Materials and Structures vol. 24, 115010, 2015, United Kingdom, 9 pages.
S.M. Corporation, "Marco Fiber Composite—MFC" Smart Material Brochure, United States, 8 pages.
Shafer, "Energy Harvesting and Wildlife Monitoring", available online at http://www.ofwin.org/wp-content/uploads/2014/11/ Shafer_keynote.pdf, 2014, 36 pages.
Brown, "Design Considerations for Piezoelectric Polymer Ultrasound Transducers", IEEE Transactions on Ultrasonics, Ferroelectrics, and Frequency Control vol. 47, No. 6, Nov. 2000, United States, pp. 1377-1396.
Brown, "The Effects of Material Selection for Backing and Wear Protection/Quarter-Wave Matching of Piezoelectric Polymer Ultrasound Transducers", IEEE Ultrasonics Symposium, 2000, United States, pp. 1029-1032.
Butler et al., "A Tri-Model Directional Modem Transducer", Oceans 2003 MTS/IEEE Conference, Sep. 22-26, 2003, United States, pp. 1554-1560.
Cada, "The Development of Advanced Hydroelectric Turbines to Improve Fish Passage Survival", Fisheries vol. 26, No. 9, Sep. 2001, United States, pp. 14-23.

Carlson et al., "Juvenile Salmon Acoustic Telemetry System Transmitter Downsize Assessment", Pacific Northwest National Laboratory, Richland, WA, 2010, United States, 30 pages.
Carlson et al., "Sensor Fish Characterization of Spillway Conditions at Ice Harbor Dam in 2004, 2005 and 2006", PNWD-3839 Final Report, Mar. 2008, United States, 95 pages.
Carlson et al., "The Sensor Fish—Making Dams More Salmon-Friendly", Sensors Online, Jul. 2004, United States, 7 pages.
Coutant, "Fish Behavior in Relation to Passage Through Hydropower Turbines: A Review", Transactions of the American Fisheries Society vol. 129, 2000, United States, pp. 351-380.
Deng et al., "Design and Implementation of a New Autonomous Sensor Fish to Support Advanced Hydropower Development", Review of Scientific Instruments vol. 85, 2014, United States, 6 pages.
Deng et al., "Evaluation of Fish-Injury Mechanisms During Exposure to Turbulent Shear Flow", Canadian Journal of Fishers and Aquatic Sciences vol. 62, 2005, Canada, pp. 1513-1522.
Deng et al., "Six-Degree-of-Freedom Sensor Fish Design and Instrument", Sensors vol. 7, 2007, United States, pp. 3399-3415.
Deng et al., "Use of an Autonomous Sensor to Evaluate the Biological Performance of the Advanced Turbine at Wanapum Dam", Journal of Renewable and Sustainable Energy vol. 2, 2010, United States, 11 pages.
Dillon, "Use and Calibration of the Internal Temperature Indicator", Microchip Technology Inc. AN1333, 2010, United States, 12 pages.
Dinwoodle, "Dual Output Boost Converter", Texas Instruments Application Report SLUA288, available online at http://www.ti.com/lit/an/slua288.pdf, Apr. 2003, 9 pages.
El Rifal et al., "Modeling of Piezoelectric Tube Actuators", Dspace@MIT: Innovation in Manufacturing Systems and Technology (IMST), 2004, Singapore, 9 pages.
Johnson et al., "A Digital Acoustic Recording Tag for Measuring the Response of Wild Marine Mammals to Sound", IEEE Journal of Oceanic Engineering vol. 28, No. 1, Jan. 2003, United States, pp. 3-12.
Kogan et al., "Acoustic Concentration of Particles in Piezoelectric Tubes: Theoretical Modeling of the Effect of Cavity Shape and Symmetry Breaking", The Journal of the Acoustical Society of America vol. 116, No. 4, 2004, United States, pp. 1967-1974.
Lewandowski et al., "In Vivo Demonstration of a Self-Sustaining, Implantable, Stimulated-Muscle-Powered Piezoelectric Generator Protoype", Annals of Biomedical Engineering vol. 37, No. 11, Nov. 2009, Netherlands, pp. 2390-2401.
Odeh, "A Summary of Environmentally Friendly Turbine Design Concepts", DOE/IS/13741 Paper, Jul. 1999, United States, 47 pages.
Pacific Northwest National Laboratory, "JSATS Tag Downsize Projects Progess Report", PNNL, Apr. 26, 2010, United States, 16 pages.
Pacific Northwest National Laboratory, "Juvenile Salmon Acoustic Telemetry System (JSATS) Acoustic Transmitters", PNNL, Mar. 2010, United States, 1 pages.
Platt et al., "The Use of Piezoelectric Ceramics for Electric Power Generation Within Orthopedic Implants", IEEE/ASME Transactions on Mechatronics vol. 10, No. 4, Aug. 2005, United States, pp. 455-461.
Richmond et al., "Response Relationships Between Juvenile Salmon and an Autonomous Sensor in Turbulent Flow", Fisheries Research vol. 97, 2009, Netherlands, pp. 134-139.
Rifai et al., "Modeling of Piezoelectric Tube Actuators", Dspace@MIT, available online at http://dspace.mit.edu/bitstream/handle/1721.1/3911/IMST014.pdf, 2004, 8 pages.

* cited by examiner

ACOUSTIC TRANSMISSION DEVICE AND PROCESS FOR TRACKING SELECTED HOSTS

STATEMENT REGARDING RIGHTS TO INVENTION MADE UNDER FEDERALLY-SPONSORED RESEARCH AND DEVELOPMENT

This invention was made with Government support under Contract DE-AC05-76RLO1830 awarded by the U.S. Department of Energy. The Government has certain rights in the invention.

FIELD OF THE INVENTION

The present invention relates generally to acoustic tracking devices and systems. More particularly, the present invention relates to attachable acoustic transmission devices for detection and remote tracking of smaller hosts both inanimate and animate in up to three dimensions in real-time or as a function of time.

BACKGROUND OF THE INVENTION

Acoustic telemetry involves acoustic devices (or tags) commonly used to monitor behavior of fish. Acoustic tags transmit a sound signal that transmits identification, location, and other information about a tagged fish to a receiver at a selected pulse rate interval (PRI), or "ping" rate. The receiver detects signals emitted by the acoustic tag and converts the sound signals into digital data. Post-processing software then processes the digital data and provides location information about the tag and thus the behavior of the fish when the receiver detects the sound signal. By identifying the signature of the acoustic signal a specific animal may be identified, which allows tracking the behavior of the host. Acoustic data may be used, e.g., to estimate survival of fish through dams and other routes of passage. However, conventional transmitters are too large for small hosts (30-100 g mass and 180-270 mm length), have short lifetimes, and/or have an inadequate transmission range that to date have precluded intensive research of small hosts such as juvenile sturgeon using acoustic telemetry techniques. Recently, an injectable acoustic tag was developed for the U.S. Army Corps of Engineers for tracking juvenile salmon detailed in U.S. patent application Ser. No. 14/014,035 filed 29 Aug. 2013, and other acoustic tags for tracking other small hosts detailed in Patent Application No.: PCT/US14/53578 filed 29 Aug. 2014, which references are incorporated herein in their entirety. The injectable acoustic tag works well for tracking yearling Chinook salmon in river systems. However, it is not optimal for long-term monitoring of hosts requiring a stronger acoustic signal and longer service life including, e.g., juvenile (<1 year old) sturgeon. Accordingly, new tag designs are needed that reduce the overall size, mass, and/or volume, that enhance the power source voltage, tag lifetimes, and transmission range, and reduce adverse effects and costs associated with attachment (which includes implantation) thus broadening the range of potential applications including, e.g., investigating behavior and habitat of juvenile sturgeon and other small species. The present invention addresses these needs.

SUMMARY OF THE INVENTION

The present invention includes a new acoustic transmission device (acoustic tag) and a process for remotely tracking various hosts in up to three dimensions in real-time or as a function of time. The acoustic tag may include a power source that delivers a power source voltage to power a tag circuit. The tag circuit may deliver a selected voltage to a piezoelectric transducer (PZT) that transmits an acoustic transmission signal at a signal intensity selected between about 159 dB and about 163 dB. The tag may be configured to provide a selectable tag lifetime at the selected signal intensity of at least about 98 days at a pulse rate interval of about 5 seconds.

The present invention also includes a method for tracking selected hosts. The method may include delivering a selected voltage from a tag circuit powered by a power source to PZT in the acoustic transmission (tag) device. The tag device may be attached to the selected host. The tag circuit may generate an acoustic transmission signal in the PZT at a selected signal intensity over a selectable tag lifetime. Signal intensity may be selected between about 159 dB and about 163 dB.

In some embodiments, the tag lifetime may be at least about 365 days at a transmission (ping) rate of about 15 seconds at a signal intensity of 161 dB.

In some embodiments, the tag lifetime may be at least about 249 days at a transmission (ping) rate of 10 seconds at a signal intensity of 161 dB.

In some embodiments, the tag lifetime may be about 156 days at a pulse rate interval of about 5 seconds and an acoustic signal intensity of 159 dB.

In some embodiments, the acoustic tag may include a power source that delivers a selectable power source voltage that powers components of the acoustic tag located on, or coupled to, a tag circuit. In various embodiments, the power source voltage may be selected between about 1.8 V and about 3.0 V.

In some embodiments, the tag circuit may include a dual boost converter sub-circuit that couples to two analog switches. In some embodiments, one of the analog switches may be coupled to the PZT through an inductor. The other analog switch may be coupled directly to the PZT. This configuration allows a higher peak-to-peak voltage from the tag circuit to be delivered across the PZT than would normally be delivered to the PZT. In some embodiments, the two analog switches may be directly coupled to the PZT, which permits the voltage from the tag circuit to be directly applied to the PZT.

In some embodiments, the dual boost converter sub-circuit may transform the voltage delivered from the power source into two output voltages. One output voltage may be a higher voltage (e.g., about +7 volts) than the power source voltage. The other output voltage may be a lower voltage (e.g., about −3 volts) than the power source voltage. The dual boost converter sub-circuit may share a single inductor to reduce the size of the tag.

The dual boost converter sub-circuit may alternately switch between the two voltage potentials in succession and deliver the two voltages through the respective analog switches to generate a selectable output voltage from the tag circuit to the PZT that drives transmission of the acoustic signal from the acoustic tag. In the exemplary embodiment, when the two voltage potentials delivered by the dual boost converter sub-circuit alternate between about +7 volts and about −3 volts, the voltage delivered from the tag circuit to the PZT may be about 20 volts (peak-to-peak).

The method may include delivering the selected (drive) voltage from the tag circuit from a boost conversion sub-circuit within the tag circuit across an inductor to the PZT.

In some embodiments, the energy expenditure for transmission of the acoustic signal from the piezoelectric transducer may be less than or equal to about 385 µJ per transmission at a signal intensity of 163 dB.

In some embodiments, the energy expenditure for transmission of the acoustic signal from the piezoelectric transducer may be less than or equal to about 283 µJ per transmission at a signal intensity of 161 dB.

In some embodiments, the acoustic signal may include a transmission range of at least about 500 meters at full intensity.

In some embodiments, the new acoustic device (tag) may include a length at or below about 24.2 mm, a diameter at or below about 5.0 mm, and a dry weight of less than about 0.72 grams.

The method may include attaching the acoustic tag to the selected host at a selected location.

The acoustic signal may be encoded with one or more tag codes of a selected code length. The acoustic signal may contain location data, identification data about the host, and/or sensor data that may all be transmitted from the acoustic tag to a receiver located external to the host.

The method may also include decoding the acoustic signal received from the acoustic tag to identify and track the host in up to three dimensions in real-time or as a function of time.

The acoustic transmission device may be configured for tracking a sturgeon host or another underwater host.

The foregoing summary is neither intended to define the invention of the application, which is measured by the claims, nor is it intended to be limiting as to the scope of the invention in any way.

DETAILED DESCRIPTION

A new acoustic transmission (tag) device and process are disclosed for identification and remote tracking of various small hosts including, e.g., juvenile sturgeon, and other deep-water and underwater hosts in up to three dimensions (3D) (i.e., X-Y-Z coordinates). In the following description, embodiments of the present invention are described by way of illustration of the best mode contemplated for carrying out the invention. Various components including, e.g., a transducer, tag and drive circuitry, and a power source are described that address specific performance requirements (e.g., size, mass, signal intensity, range, and tag lifetime). It will be apparent that the invention is amenable to various permutations, modifications, and alternative constructions. It should be understood that there is no intention to limit the present invention to specific forms disclosed herein, but, on the contrary, the present invention is to intended cover all modifications, alternative constructions, and equivalents falling within the scope of the present invention as defined in the claims. Therefore the description should be seen as illustrative and not limiting.

Acoustic tags of the present invention may include various form factors and shapes that allow the tags to be attached to selected hosts for selected applications. However, shapes are not intended to be limited. The term "form factor" used herein refers to the physical arrangement, configuration, and dimensions of electrical components in the acoustic tags and the capsule that contains the device components. The term "host" refers to inanimate or animate objects to which the acoustic tag may be attached for tracking and/or identification. Inanimate hosts include, but are not limited to, e.g., propelled objects (e.g., robots), stationary objects, movable objects, and transportable objects. Animate hosts may include, but are not limited to, e.g., aquatic species including, e.g., marine and freshwater animals, deep water hosts (e.g., juvenile sturgeon, lamprey, and eels), divers, underwater mammals, and other living hosts. The present invention will now be described with reference to tracking of an exemplary deep-water host, i.e., juvenile sturgeon. However, it should be understood that the invention is not intended to be limited thereto. As discussed above, acoustic tags of the present invention are well suited for a wide variety of applications and tracking of different hosts. No limitations are intended.

Figure 1:
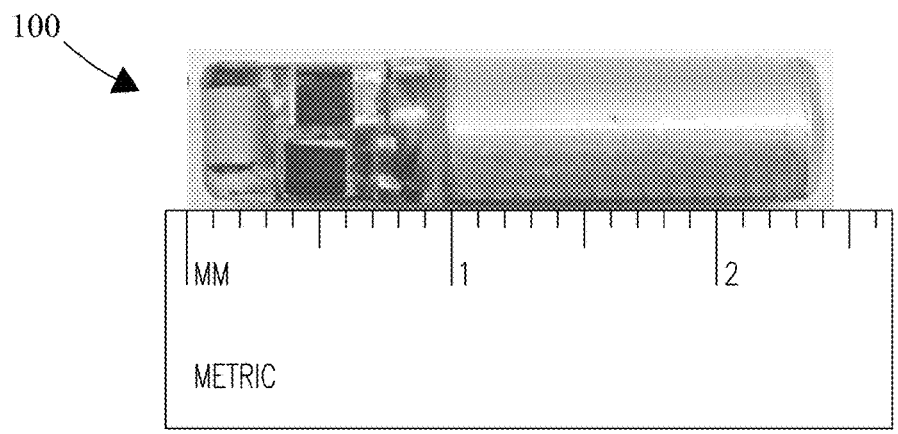
FIG. 1 shows an acoustic transmission device of the present invention and associated length dimensions.

FIG. 1 is a perspective view of a new acoustic transmission device (acoustic tag) 100 of the present invention. In the exemplary embodiment, acoustic tag 100 may include an elongated or cylindrical shape that permits the tag to be easily implanted in, or attached to, the selected host. Approaches for attachment are not limited. TABLE 1 lists exemplary parameters of the new acoustic tag.

TABLE 1

| | |
|---|---|
| Dimensions (Length × Diameter): | 24.2 mm × Ø5.0 mm* |
| Dry Weight: | 720 mg |
| Volume: | 429 mm$^3$ |
| Source Level: | 159-163 dB (re: 1 µPa @ 1 meter) |
| Tag lifetime: | 98-156 days at 5-second pulse rate interval (163 dB and 159 dB, respectively) |
| Tag lifetime: | 285-365 days at 15-second pulse rate interval (163 dB and 161 dB, respectively) |
| Transmission Range: | Up to 500 meters (163 dB) |

*Ø is an engineering unit for diameter, given here in millimeters.

In the exemplary embodiment, tag 100 may include a length of 24.2 mm and a maximum diameter of 5.0 mm. The front end of the tag may include a narrower dimension than the back end of the tag and may include a relatively flat profile to minimize weight of the tag. The acoustic tag includes a compact volume, and a mass of about 720 mg in air. Tag 100 further includes a unique tag circuit that drives transmission of the acoustic signal from the PZT, a power source with a greater power output, an enhanced and adjustable acoustic signal intensity (or source level), a selectable and longer tag lifetime, and a longer transmission range for tracking selected hosts. The acoustic transmission signal may be adjusted to provide various detection ranges and tag lifetimes.

Figure 2:
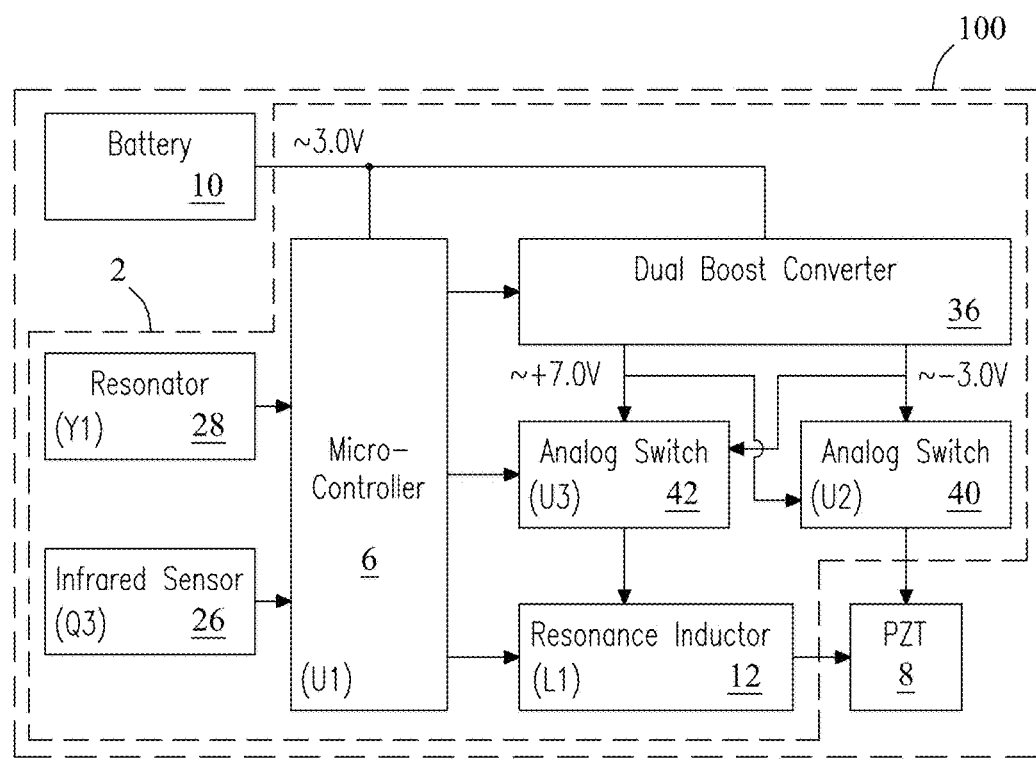
FIG. 2 is a block diagram showing components of the acoustic transmission device.

FIG. 2 is a block diagram showing exemplary components of acoustic tag 100 of the present invention and associated electrical inputs and outputs. Tag 100 may include a power source (e.g., battery) 10 that powers components of the acoustic tag. Power source 10 may be a custom lithium carbon fluoride battery of a similar design to that described in U.S. application Ser. No. 14/014,035. Each laminate may include an anode and a cathode positioned between polymer separators that electrically isolate the cathode from the anode in the laminate. The separator may include micro-porous polypropylene. The cathode may include, or be constructed of, e.g., carbon fluoride and a conducting carbon within a binder affixed at a selected thickness to a current collector. The binder may include, e.g., polytetrafluoroethylene (PTFE). The anode may be constructed of lithium metal. The power source may be filled with an electrolyte such as, e.g., lithium hexafluorophosphate ($LiPF_6$) disbursed in a selected volume ratio of ethylene carbonate (EC) and dimethyl carbonate (DMC). In the exemplary embodiment, power source may be of a larger size that provides a greater power output of up to about 80 mAh and a longer tag lifetime. In the instant design, power source 10 may include a plurality of laminates configured to supply a selectable output voltage between about 1.8 volts (1.8 V) to about 3.0 volts (3.0 V).

Tag 100 may also include a programmable microcontroller 6 (U1) (e.g., a model PIC16F1823T/CL 8-bit, 8K flash, programmable microcontroller in a chip-scale package, Microchip Technology, Chandler, Ariz., USA) that provides operational control of components of acoustic tag 100. Tag components are configured to generate and deliver an acoustic signal at a desired modulation or resonance frequency (e.g., 416.7 kHz) that is transmitted from the acoustic tag.

Resonator 28 (Y1) (e.g., a model CSTCE10M0G52-R0, 10 MHz ceramic resonator, Murata Manufacturing Co., Ltd., Nagaokakyo, Kyoto Prefecture, Japan) may be coupled on the input side of microcontroller 6 (U1) to generate a clock signal of a selected precision (e.g., ±0.5% tolerance or better) that controls operation of controller (U1) 6 and other components of acoustic tag 100.

A phototransistor (Q3) 26 (e.g., a model PT19-21B, flat black mini SMD phototransistor, Everlight Electronics Co., Ltd., New Taipei City, Taiwan) sensitive to optical or infrared radiation may be coupled on the input side of microcontroller 6 to receive configuration commands from an external computer.

Tag 100 may further include a dual boost converter sub-circuit 36 that couples to two analog switches 40 (U2) and 42 (U3). Analog switch 42 (U3) may be coupled to a high-efficiency resonance inductor 12 (L1) (e.g., a 10 uH, 80 MAmp, 20% tolerance inductor, Coilcraft, Cary, Ill., USA). Analog switch 40 (U2) and resonance inductor 12 (L1) may be coupled to piezoelectric transducer 8. The dual boost converter sub-circuit, two analog switches, and resonance inductor together generate a drive voltage that drives transmission of the acoustic signal from piezoelectric transducer 8 at a selected modulation or resonance frequency, e.g., 416.7 kHz.

Dual boost converter sub-circuit 36 also controls the intensity of the acoustic signal delivered from piezoelectric transducer 8. The signal intensity is selectable between about 159 dB and about 163 dB. Selection of the power source voltage and the acoustic signal intensity provides a selectable tag lifetime.

Figure 3A:
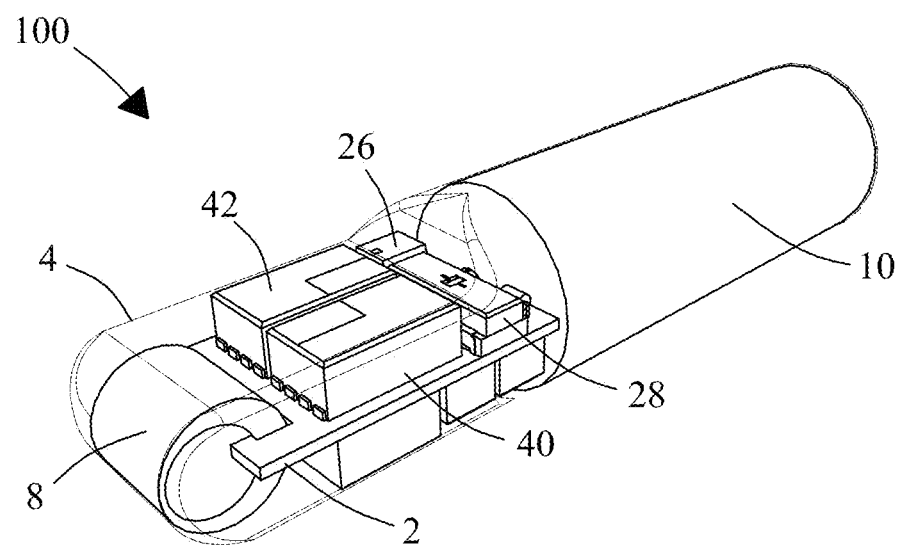
FIGS. 3A-3B are different top views of the present invention.
Figure 4A:
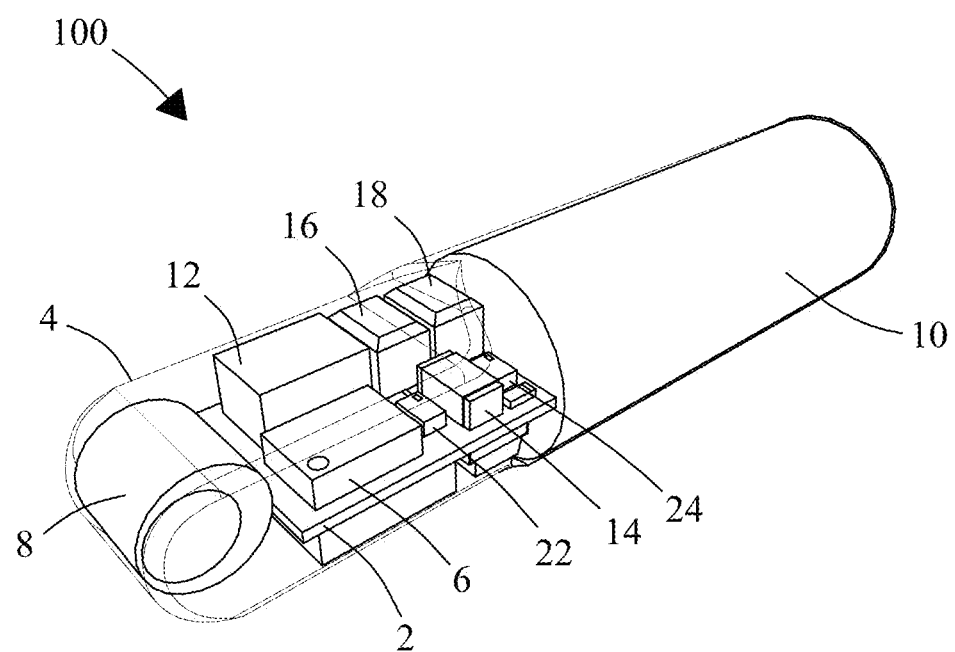
FIGS. 4A-4B are different bottom views of the present invention.

Components of tag 100 may be selected to reduce physical dimensions and weight of the tag, and may be coupled to both sides of a circuit board 2 as shown in FIG. 3A and FIG. 4A described hereafter. Circuit board 2 may be constructed of rigid board materials (~0.02 cm thickness) such as FR4 boards, or flexible board materials (~0.01 cm thickness) such as flex boards.

Figure 3B:
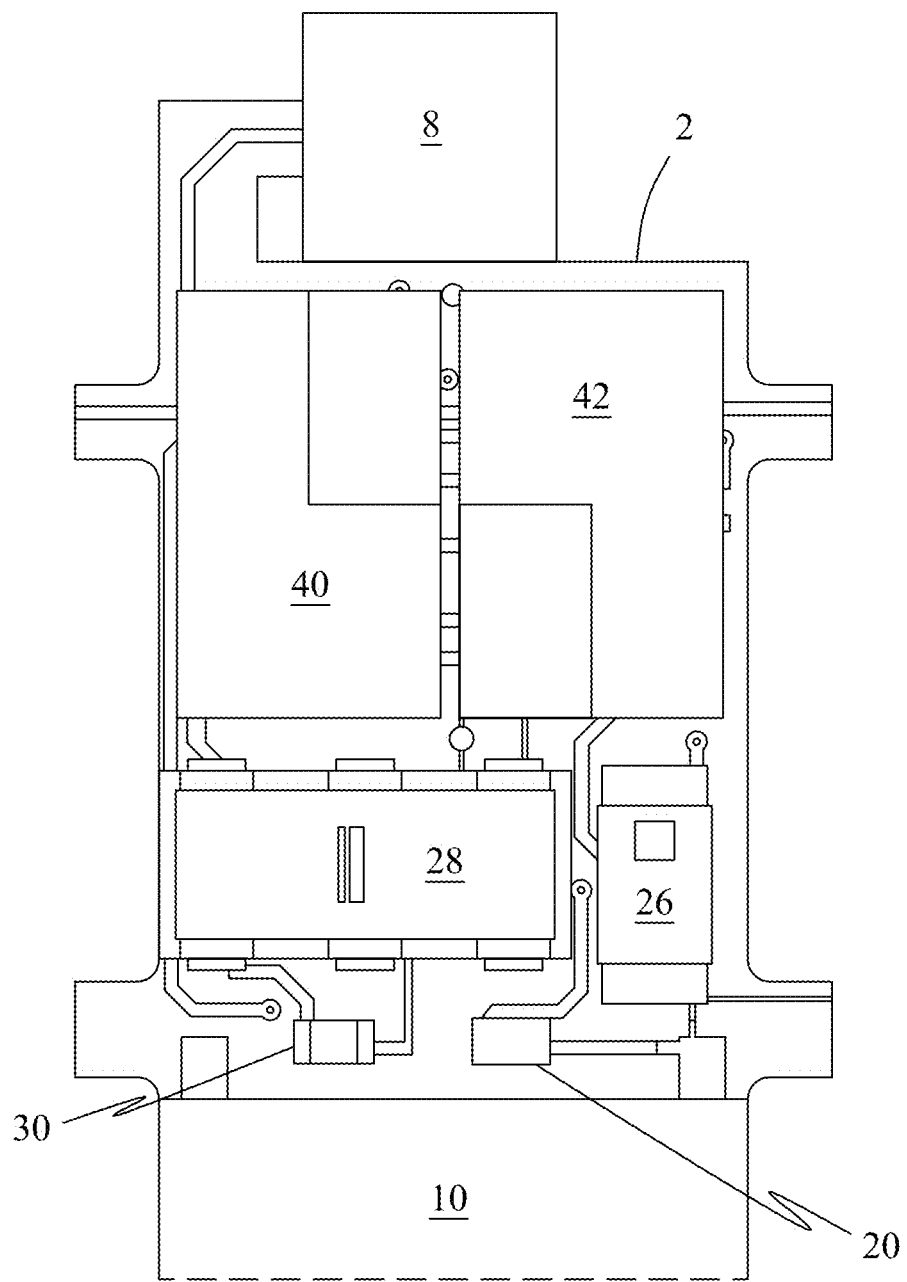

FIGS. 3A-3B present different top-side views of circuit board 2 showing position of selected components of acoustic tag 100. In these figures, piezoelectric transducer 8 is shown electrically coupled to circuit board 2, e.g., at a forward end of acoustic tag 100 such that the acoustic signal may be transmitted free of interference from or obstruction by other tag components. Power source 10 may be coupled to circuit board 2 at an end opposite piezoelectric transducer 8 to power operation of piezoelectric transducer 8 and other tag components. However, location is not intended to be limited.

Resonator 28 (Y1) (e.g., a 10 MHz ceramic resonator described previously in reference to FIG. 2) may be coupled to microcontroller 6 to control timing of operation of tag components. Phototransistor 26 (Q3) may be positioned to receive configuration commands from a source computer. Analog switches 40 (U2) and 42 (U3) may be positioned to deliver a drive voltage to PZT 8 of about 20 volts (peak-to-peak) directly to piezoelectric transducer 8, or to deliver the same drive voltage across a resonance inductor 12 (L1) to piezoelectric transducer 8 as described previously herein.

Tag 100 components may be encapsulated within a coating composed of a thermosetting polymer such as an epoxy (e.g., EPO-TEK® 301 epoxy, Epoxy Technology Inc., Bellerica, Mass., USA) or a resin (e.g., Scotchcast® Electrical Resin 5, 3M Company, St. Paul, Minn., USA) that forms a capsule 4.

In FIG. 3B, a resistor 30 (R1) (e.g., a 1.0 Mohm, 1/20 W, 5% tolerance, SMD resistor, Vishay Intertechnology, Inc., Malvern, Pa., USA) may be coupled in parallel with resonator 28 (Y1) to stabilize the frequency of resonator 28 (Y1).

A bypass capacitor 20 (C3) (e.g., a model CL03A105MP3NSNC, 1-μF, 10-volt, 20% tolerance, X5R dielectric, and 0201 size tantalum capacitor, Samsung Electro-Mechanics America, Inc., Irvine, Calif., USA) may be coupled to controller 6 and power source 10 to filter electronic noise and current spikes stemming from components on circuit board 2. As will be appreciated by those of ordinary skill in the art, electrical components may be positioned where needed. No limitations are intended.

Figure 4B:
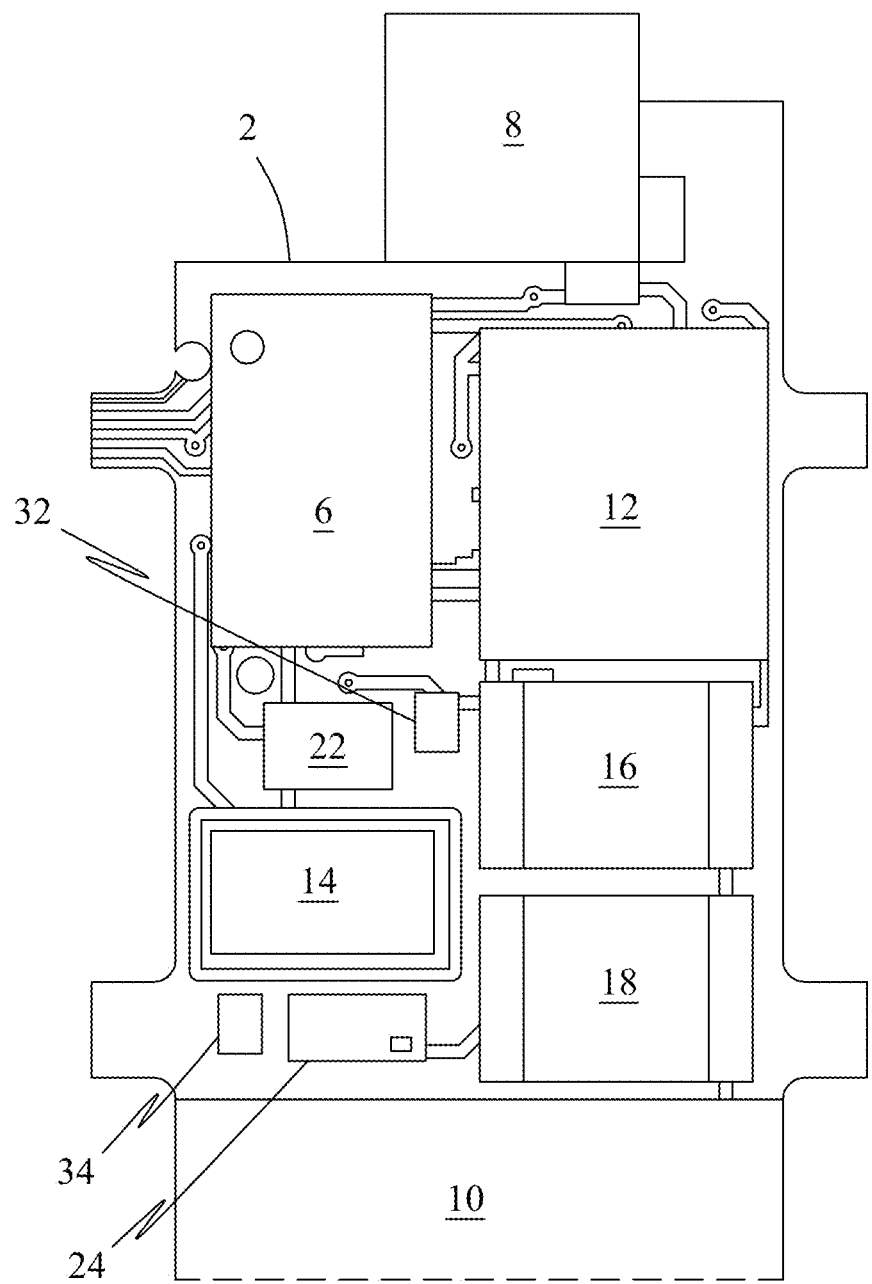

FIGS. 4A-4B are different bottom-side views of circuit board 2 showing position of selected components of acoustic tag 100. Piezoelectric transducer 8 and power source 10 may be coupled as described previously (see FIG. 3A-3B).

Microcontroller 6 (U1) may control operation of the components of the tag. In the exemplary embodiment, microcontroller 6 (U1) is shown positioned adjacent piezoelectric transducer 8, but position is not intended to be limited thereto.

A first transistor 22 (Q1) (e.g., a model PMZB350UPE-315, 20-volt, p-channel MOSFET, NXP Semiconductors, San Jose, Calif., USA), a first capacitor 16 (C1) (e.g., a 47 uF, 10-volt, 20% tolerance, X5R dielectric, and 0805 size ceramic capacitor, TDK Corp., Minato, Tokyo, JP), and an inductor 14 (L2) (e.g., a 10 uH, 80 MAmp, 20% tolerance, and 0603 size inductor, TDK Corp., Minato, Tokyo, JP) are components of the dual boost converter sub-circuit 36. These components generate the negative output voltage (e.g., about −3 volts), and couple electrically to analog switches 40 (U2) and 42 (U3) described previously in reference to FIG. 2 and FIGS. 3A-3B.

A second transistor 24 (Q2) (e.g., a 30-volt, 1.78 A, N-channel MOSFET, Fairchild Semiconductor, Inc., Dallas, Tex., USA) and a second capacitor 18 (C2) (e.g., a 47 uF, 10-volt, 20% tolerance, X5R dielectric, and 0805 size ceramic capacitor, TDK Corp., Minato, Tokyo, JP), are additional components of the dual boost converter sub-circuit 36. These components share inductor 14 (L2) described previously above and together generate the positive output voltage (e.g., about +7 volts), and couple electrically to analog switches 40 (U2) and 42 (U3) described previously in reference to FIG. 2 and FIGS. 3A-3B.

Analog switch 42 (U3) may couple to piezoelectric transducer 8 through inductor 12 (L1) to increase the drive voltage across the piezoelectric transducer.

In FIG. 4B, a first diode 32 (D1) (e.g., a 30-volt, 0.1 A, 2DFN Schottky Diode 0201, Diodes, Inc., Plano, Tex., USA) and a second diode 34 (D2) (e.g., a 30-volt, 0.1 A, 2DFN Schottky Diode 0201, Diodes, Inc., Plano, Tex., USA) are additional components of the dual boost converter sub-circuit 36. First diode 32 (D1) assists in the generation of the negative voltage (e.g., −3 volts), and second diode 34 (D2) assists in the generation of the positive voltage (e.g., +7 volts).

Tag Circuit

Figure 5:
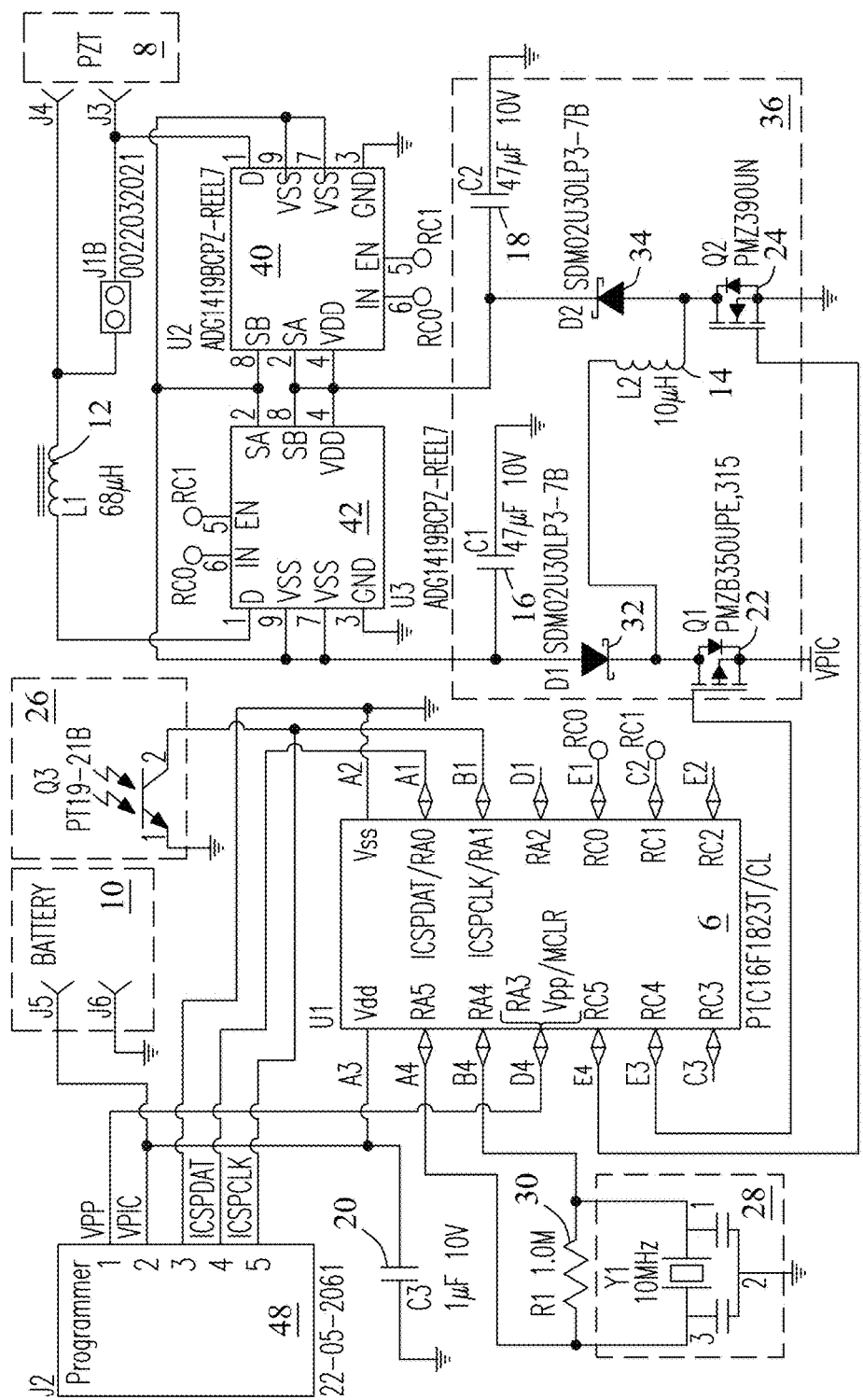
FIG. 5 shows a circuit diagram of the acoustic transmission device of the present invention.

FIG. 5 shows an exemplary tag circuit for acoustic tags of the present invention showing components described previously above. Components may be located on, or coupled to, a circuit board described previously in reference to FIG. 2. The tag circuit may include preferred trace line widths of about 0.01 cm (0.003 inches), but are not intended to be limited.

Configuration commands for programming microcontroller 6 may be received directly from an external computer (not shown), e.g., through an Integrated Circuit Serial Programmer (ICSP) module 48 (e.g. a MPLAB ICD 3 programmer, Microchip Technologies, Chandler, Ariz., USA) that couples to microcontroller 6. Programmer (ICSP) module 48 may couple to the external computer through a programming connector (e.g., a model 22-05-2061, 6-position connector, Molex Connector Corp., Lisle, Ill., USA) (not shown). The programming connector may be detached from the circuit board during assembly of the acoustic tag to reduce the final volume of the assembled tag.

Configuration and programming information may also be delivered remotely (e.g., optically) from the external computer through phototransistor 26 (Q3) and into controller 6 through a selected input pin. Pins are not intended to be limited.

Bypass capacitor 20 (C3) may be coupled to controller 6 and power source 10 to filter electronic noise and current spikes from components on the circuit board.

Resonator 28 (Y1) delivers a clock signal that controls the timing of delivery of a positive channel drive signal (PCH-DRV) and a negative channel drive signal (NCH-DRV) to dual boost converter sub-circuit 36 described hereafter. A resistor 30 (R1) may be placed in parallel with resonator 28 (Y1) to stabilize the frequency and clock signal of resonator 28 (Y1).

Dual boost converter sub-circuit 36 may include a first transistor 22 (Q1), an inductor 14 (L2), a first diode 32 (D1), and a first capacitor 16 (C1) that together generate a negative output voltage (e.g., −3 volts). Microcontroller 6 may toggle the PCH-DRV signal to alternately build up current through inductor 14 (L2), and then discharges capacitor 16 (C1) through diode 32 (D1). Magnitude of the positive output voltage depends in part on the length of time that microcontroller 6 toggles the PCH-DRV signal. Microcontroller 6 may hold the NCH-DRV signal at a positive voltage during operation so that a second transistor 24 (Q2) described hereafter can conduct current.

Dual boost converter sub-circuit 36 may include second transistor 24 (Q2), inductor 14 (L2), second diode 34 (D2), and second capacitor 18 (C2) that together generate a positive output voltage (e.g., +7 volts). Microcontroller 6 toggles the NCH-DRV signal to alternately build up current through inductor 14 (L2), and then charge capacitor 18 (C2) through diode 34 (D1). The magnitude of the positive output voltage generally depends on the length of time that the microcontroller toggles the NCH-DRV signal. Microcontroller 6 (U1) may hold the PCH-DRV signal at zero voltage during this operation so that first transistor 22 (Q1) can conduct current.

Dual boost converter sub-circuit 36 may couple to two analog switches 40 (U2) and 42 (U3). The two analog switches respectively receive the positive and negative output voltages from the dual boost converter sub-circuit 36. The analog switches switch between these two voltages alternately in succession, under the control of microcontroller 6 (U1), to generate a selected (drive) voltage from the tag circuit that is delivered to piezoelectric transducer 8. Analog switch 40 (U2) may couple to one terminal (e.g., negative terminal) of piezoelectric transducer 8. Analog switch 42 (U3) may couple through a resonance inductor 12 (L1) to another terminal (e.g., positive terminal) of piezoelectric transducer 8. The drive voltage may be delivered from analog switch 42 (U3) through resonance inductor 12 (L1) to piezoelectric transducer 8 to generate the acoustic signal transmitted from piezoelectric transducer 8. Resonance inductor 12 (L1) is configured to increase the voltage delivered at the terminals of piezoelectric transducer 8. The acoustic signal transmitted from piezoelectric transducer 8 may have a selected modulation frequency (e.g., 416.7 kHz). The value of inductor 12 (L1) may be selected such that the inductance partially or fully cancels out characteristic capacitances of piezoelectric transducer 8 at the selected modulation frequency. The resulting voltage at each terminal of piezoelectric transducer 8 may go above the positive drive voltage and below the negative drive voltage. As will be appreciated by those of ordinary skill in the art, modulation frequencies may be varied and hence are not intended to be limited to the exemplary value described herein.

Tag Lifetimes

Lifetimes of acoustic tags of the present invention depend in part on the size of the power source (battery) 10 described previously in reference to FIG. 5. However, for a given power source size, in general, tag lifetimes are selectable by selecting: 1) the PRI for transmission of the acoustic signal, 2) the intensity of the acoustic signal, or 3) both the PRI and the intensity of the acoustic signal.

Within the selectable range of acoustic intensity between about 159 dB and about 163 dB, tag lifetimes may be estimated from empirical equation [1]:

$$T = \frac{V_{batt} * C_{batt} * t_0 * 1000}{130 + 35 * 10^{\frac{SL-155}{10}} + V_{batt} * I_S * t_0} * \frac{1}{24} \quad [1]$$

Here, lifetime (T) has units of days. ($V_{batt}$) is the battery voltage and has units of volts. ($C_{batt}$) is the battery capacity in units of milli-Amp-Hours (mAh). (SL) is the acoustic intensity (or source level) in units of dB. ($I_s$) is the constant static current that flows through the tag circuit (FIG. 5) in units of micro-Amps. ($t_0$) is the PRI in units of seconds. TABLE 2 lists exemplary constants that may be employed for calculating tag lifetimes (T) at a PRI ($t_0$) of 5 seconds and a signal strength (intensity) of 163 dB:

TABLE 2

| Item | Values |
|---|---|
| $V_{batt}$ | 3.0 V |
| $C_{batt}$ | 56 mAh |
| SL | 163 dB |
| $t_0$ | 5 seconds |
| $I_s$ | 0.4 μA |

From Equation [1], tag lifetime (T) may be calculated at about 98 days using identified variable values. Acoustic tags of the present invention are configured to maintain a selected energy expenditure ($e_{pulse}$) for each transmission of the acoustic signal even as battery voltage decreases gradually over time. Energy expenditure ($e_{pulse}$) values may be less than or equal to about 385 μJ per transmission at a signal intensity of 163 dB, and less than or equal to about 283 μJ per transmission at a signal intensity of 161 dB.

Actual tag lifetimes (T) may be longer than calculated lifetimes based on nominal energy expenditure ($e_{pulse}$) values. As an example, at a signal intensity (strength) setting of 163 dB, an empirical energy consumption value of 351 μJ per transmission may be used instead of the nominal 385 μJ for a more accurate estimate of tag lifetime. In another example, at a signal strength setting of 161 dB, an empirical energy consumption value of 269 μJ may be used instead of the nominal 283 μJ.

TABLE 3 lists experimental and projected tag lifetimes for acoustic tags of the present invention at selected PRIs and selected signal intensities.

TABLE 3

| | | PRI ($t_0$) (seconds) | | | | |
|---|---|---|---|---|---|---|
| | | 0.5 | 1 | 5 | 10 | 15 |
| Tag Lifetime (T) (days) | @163 dB | 8.9 | 19.9 | 98 | 193 | 285 |
| | @161 dB | 12.9 | 25.9 | 127 | 249 | 365 |
| Note: | | Experimental values | | Projected values | | |

Lifetimes (T) of acoustic tags of the present invention are selectable. Shorter tag lifetimes and longer tag lifetimes may be selected. In the table, it can be seen that for a selected signal intensity, tag lifetime may be selected by varying the PRI. For example, at a signal intensity of 163 dB, tag lifetime corresponding to a 5 sec PRI is about 98 days; tag lifetime corresponding to a 15 sec PRI is about 285 days. It will be readily understood by those of ordinary skill in the art that various signal intensities may be selected with their corresponding lifetimes at selected PRIs to meet specific tracking needs for selected hosts and/or for selected applications. No limitations are intended. For example, for a tag with a signal intensity set at 161 dB, tag lifetime may be at least about 12.9 days using a PRI of 0.5 seconds, at least about 127 days using a PRI of 5 seconds, or about 365 days using a PRI of 15 seconds.

Beam Transmission Patterns

Beam transmission patterns of the piezoelectric transducer are described, e.g., in U.S. application Ser. No. 14/014,035 filed 29 Aug. 2013.

Transmission Detection Range

Acoustic signals transmitted by tags of the present invention may include selected detection ranges. Tag signals may be encoded to provide maximum strength and to improve range and resolution. In locations with a relatively small amount of background noise, such as the middle of a lake, signals may be transmitted up to about 500 meters. The present tag delivers a higher source level output to provide for the 500-meter detection range than used in previous tags. TABLE 4 lists projected detection ranges at two exemplary intensity values of 163 dB and 161 dB for three different signal transmission spread scenarios and an assumed noise level of 97 dB in a quiet environment (e.g. the forebay of a dam). However, no limitations are intended by the illustrative example.

TABLE 4

| | | Detection range (meters) | | |
|---|---|---|---|---|
| | | Spherical | Realistic* | Cylindrical |
| Forebay | @163 dB | 726 | 512 | 770 |
| | @161 dB | 249 | 475 | 277 |

*A noise level of 97 dB is presumed based on actual noise level measurements.

Data suggest a transmission detection range of 500 meters or better may be achieved at an acoustic signal intensity selected from 159 dB to 163 dB. In locations with larger background noise (e.g., immediately downstream of a dam spillway), signals may be transmitted about 100 meters. However, distances are not intended to be limited.

Coding and Activation

Tags of the present invention may be programmed with one or more tag codes of a selectable code length. The microcontroller (FIG. 2) may also contain internal sensors such as temperature sensors that collect additional data from the host and surrounding environment. As an example, a 5-bit temperature value or other sensor values with selected bit-lengths may be input from selected sensors into one or more tag codes that are then transmitted from the piezoelectric transducer. Coding and sensors are described in U.S. application Ser. No. 14/014,035 filed 29 Aug. 2013.

Methods and locations for attachment of acoustic tags to selected hosts are not limited. Acoustic tags may be attached, e.g., to the outside of the host (e.g., to the clothing or scuba gear of a human host), to an inanimate object, to a self-propelled object such as a robot, attached internally to the host (e.g., inserted within an object, surgically implanted, or injected). No limitations are intended.

Applications for acoustic tags of the present invention may include, but are not limited to, e.g., survival studies; monitoring migration/passage/trajectories; tracking host behavior or location in two dimensions (2D) or three dimensions (3D); measuring bypass effectiveness at dams and other passages; observing predator/prey dynamics; helping public utility agencies, private firms, and state and federal agencies meet fishery or other regulations; and other applications. Applications are not intended to be limited.

The present invention delivers unsurpassed advantages not obtained in previous designs and open up a broad array of tag uses and applications not yet realized. The high-efficiency piezoelectric transducer drive circuit in the instant design enhances energy conversion efficiency and reduces number of dedicated components, all while maintaining the same source level performance. Fewer components decreases the energy required to power the tag, which permits yet smaller acoustic tags with a lower mass to be constructed for even smaller hosts and applications.

While the invention has been described with what is presently considered to be the most practical and preferred embodiments, many changes, modifications, and equivalent arrangements may be made without departing from the invention in its true scope and broader aspects. Thus, the scope is expected to be accorded the broadest interpretation relative to the appended claims. The appended claims are therefore intended to cover all such changes, modifications, equivalent structures, and products as fall within the scope of the invention. No limitations are intended.

What is claimed is:

1. An acoustic transmission (tag) device, comprising:
a power source;
a tag circuit;
a piezoelectric transducer;
a housing configured to be associated with a host to be tracked and wherein the housing is coupled with the power source, the tag circuit and the piezoelectric transducer; and
wherein the power source delivers a power source voltage to power the tag circuit, and the tag circuit delivers a selected voltage to the piezoelectric transducer that transmits an acoustic transmission signal at a selected signal intensity between about 159 dB and about 163 dB.

2. The acoustic device of claim 1, wherein the tag is configured to provide a tag lifetime of at least about 365 days at a pulse rate interval of about 15 seconds and a signal intensity of 161 dB.

3. The acoustic device of claim 1, wherein the tag circuit includes a dual boost converter sub-circuit that couples to two analog switches that deliver the selected voltage to the piezoelectric transducer.

4. The acoustic device of claim 1, wherein the tag circuit includes a dual boost converter sub-circuit that generates voltage potentials that alternate between about −3 volts and about +7 volts.

5. The acoustic device of claim 1, wherein the tag circuit delivers a selected voltage delivered to the piezoelectric transducer that is at least about 20 volts (peak-to-peak).

6. The acoustic device of claim 1, wherein the power source delivers a selectable power source voltage between about 1.8 V to about 3.0 V.

7. The acoustic device of claim 1, wherein the tag circuit expends an energy for transmission of the acoustic signal from the piezoelectric transducer of less than or equal to about 283 µJ per transmission at a signal intensity of 161 dB.

8. The acoustic device of claim 1, wherein the tag circuit expends an energy for transmission of the acoustic signal from the piezoelectric transducer of less than or equal to about 385 µJ per transmission at a signal intensity of 163 dB.

9. The acoustic device of claim 1, wherein the piezoelectric transducer delivers the acoustic signal over a transmission range up to at least about 500 meters at full intensity.

10. A method for tracking a selected host, comprising the steps of:
associating an acoustic transmission (tag) device with a selected host to be tracked;
while the acoustic transmission (tag) device is associated with the host, delivering a selected voltage from a tag circuit powered by a power source to a piezoelectric transducer in the acoustic transmission (tag) device to generate an acoustic transmission signal therein;
while the acoustic transmission (tag) device is associated with the host, transmitting the acoustic transmission signal from the piezoelectric transducer at a selected signal intensity between about 159 dB and about 163 dB to track the selected host; and
while the acoustic transmission (tag) device is associated with the host, transmitting the acoustic transmission signal externally of the host.

11. The method of claim 10, wherein transmitting the acoustic transmission signal includes a tag lifetime of at least about 365 days at a pulse rate interval of about 15 seconds at a signal intensity of 161 dB.

12. The method of claim 10, wherein delivering the selected voltage from the tag circuit includes generating the voltage in a dual boost converter sub-circuit that couples to two analog switches within the tag circuit.

13. The method of claim 10, wherein delivering the selected voltage from the tag circuit includes generating voltage potentials in a dual boost converter sub-circuit that alternates between about −3 volts and about +7 volts.

14. The method of claim 10, wherein delivering the selected voltage from the tag circuit includes a voltage of at least about 20 volts (peak-to-peak).

15. The method of claim 10, wherein delivering the selected voltage from the tag circuit includes delivering a power source voltage from the power source selected between about 1.8 V to about 3.0 V.

16. The method of claim 10, wherein transmitting the acoustic signal includes an energy expenditure by the tag circuit of less than or equal to about 283 µJ per transmission at a signal intensity of 161 dB.

17. The method of claim 10, wherein transmitting the acoustic signal includes an energy expenditure by the tag circuit of less than or equal to about 385 uJ per transmission at a signal intensity of 163 dB.

18. An acoustic transmission (tag) device, comprising:
a tag circuit comprising components that deliver a selectable voltage to a piezoelectric transducer that drives transmission of an acoustic transmission signal therefrom at a selected acoustic signal intensity; and
a power source coupled to the tag circuit and which is configured to deliver a selectable power source voltage that powers the components of the tag circuit over a selectable tag lifetime of at least about 98 days at a pulse rate interval of about 5 seconds at an acoustic signal intensity of 163 dB.

19. The acoustic device of claim 1, wherein the tag is configured to provide a selectable tag lifetime at the selected signal intensity of at least about 98 days at a pulse rate interval of about 5 seconds.

20. The method of claim 10, wherein transmitting the acoustic transmission signal includes a tag lifetime of at least about 98 days at a pulse rate interval of about 5 seconds.

21. The acoustic device of claim 1, wherein the tag has a volume of about 429 mm³ or less.

22. The acoustic device of claim 1, wherein the tag has a mass of about 720 mg or less in air.

23. The acoustic device of claim 1, wherein the tag circuit comprises:
a dual boost converter configured to generate a negative output voltage and a positive output voltage; and
an inductor configured to increase the voltage which is delivered to the piezoelectric transducer.

24. The acoustic device of claim 23, further comprising:
a first switch coupled with the dual boost converter and a terminal of the piezoelectric transducer; and
a second switch coupled with the dual boost converter and the inductor.

25. The acoustic device of claim 1, wherein the housing is configured to be received within the host to be tracked.

26. The acoustic device of claim 1, wherein the tag circuit comprises:
   a dual boost converter configured to generate a negative output voltage and a positive output voltage; and
   an inductor between the dual boost converter and the piezoelectric transducer.

27. The acoustic device of claim 26, further comprising:
   a first switch coupled with the dual boost converter and a terminal of the piezoelectric transducer; and
   a second switch coupled with the dual boost converter and the inductor.

* * * * *

UNITED STATES PATENT AND TRADEMARK OFFICE
CERTIFICATE OF CORRECTION

PATENT NO. : 10,101,429 B2  
APPLICATION NO. : 14/631587  
DATED : October 16, 2018  
INVENTOR(S) : Zhiqun Deng et al.

Page 1 of 2

It is certified that error appears in the above-identified patent and that said Letters Patent is hereby corrected as shown below:

On the Title Page

(56) References Cited, page 2, 2nd Column, 22nd Line - Replace "EP 1705508 B1 6/2010" with --EP 1705500 B1 6/2010--

(56) References Cited, page 2, 2nd Column, 36th Line - Replace "PCT/US2016/054961" with --PCT/US2016/054981--

(56) References Cited, page 3, 1st Column, 29th Line - Replace "cation No. PCT/U52014/053578, International Filing Date Aug. 29," with --cation No. PCT/US2014/053578, International Filing Date Aug. 29,--

(56) References Cited, page 3, 2nd Column, 23rd Line - Replace "Ontario, 2012, Canada, 131 pages." with --Ontario, 2013, Canada, 131 pages.--

(56) References Cited, page 3, 2nd Column, 29th Line - Replace "Tagged with Passive Integrated Transponders (PUT) in Freshwater" with --Tagged with Passive Integrated Transponders (PIT) in Freshwater--

(56) References Cited, page 4, 2nd Column, 27th Line - Replace "Dinwoodle, "Dual Output Boost Converter", Texas Instruments" with --Dinwoodie, "Dual Output Boost Converter", Texas Instruments--

(56) References Cited, page 4, 2nd Column, 29th Line - Replace "com/lit/an/slua288.pdf, Apr. 2003, 9 pages," with --com/lit/an/slua288/slua288.pdf, Apr. 2003, 9 pages.--

(56) References Cited, page 4, 2nd Column, 30th Line - Replace "El Rifal et al., "Modeling of Piezoelectric Tube Actuators"," with --El Rifai et al., "Modeling of Piezoelectric Tube Actuators",--

Signed and Sealed this  
Sixth Day of August, 2019

Andrei Iancu  
*Director of the United States Patent and Trademark Office*

CERTIFICATE OF CORRECTION (continued)
U.S. Pat. No. 10,101,429 B2

(56) References Cited, page 4, 2nd Column, 43rd Line - Replace "Protoype", Annals of Biomedical Engineering vol. 37, No. 11, Nov." with --Prototype", Annals of Biomedical Engineering vol. 37, No. 11, Nov.--

(56) References Cited, page 4, 2nd Column, 46th Line - Replace "Concepts", DOE/IS/13741 Paper, Jul. 1999, United States, 47" with --Concepts", DOE/ID/13741 Paper, Jul. 1999, United States, 47--

UNITED STATES PATENT AND TRADEMARK OFFICE
CERTIFICATE OF CORRECTION

PATENT NO. : 10,101,429 B2
APPLICATION NO. : 14/631587
DATED : October 16, 2018
INVENTOR(S) : Zhiqun Deng et al.

It is certified that error appears in the above-identified patent and that said Letters Patent is hereby corrected as shown below:

In the Specification

Column 1, Line 10 – Replace "DE-AC05-76RLO1830" with --DE-AC05-76RL01830--

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*